(12) United States Patent
Sellinger et al.

(10) Patent No.: US 12,180,154 B2
(45) Date of Patent: Dec. 31, 2024

(54) UPGRADING STREAMS COMPRISING $C_3$ AND $C_4$ HYDROCARBONS

(71) Applicant: KELLOGG BROWN & ROOT LLC, Houston, TX (US)

(72) Inventors: David Sellinger, Houston, TX (US); Robert Choi, Houston, TX (US); Quo-Chen Yeh, Sugar Land, TX (US); Alok Srivastava, Houston, TX (US); Kristine E. Hamilton, Houston, TX (US); Michael A. Radzicki, Houston, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 17/729,937

(22) Filed: Apr. 26, 2022

(65) Prior Publication Data
US 2022/0340504 A1    Oct. 27, 2022

Related U.S. Application Data

(60) Provisional application No. 63/180,311, filed on Apr. 27, 2021.

(51) Int. Cl.
*C07C 7/167* (2006.01)
*B01J 19/00* (2006.01)
(Continued)

(52) U.S. Cl.
CPC .......... *C07C 7/167* (2013.01); *B01J 19/0013* (2013.01); *C07C 5/09* (2013.01); *C07C 11/167* (2013.01); *B01J 2219/00051* (2013.01)

(58) Field of Classification Search
None
See application file for complete search history.

(56) References Cited

U.S. PATENT DOCUMENTS

| | | | |
|---|---|---|---|
| 3,075,917 A * | 1/1963 | Kronig | C07C 5/03 208/143 |
| 4,802,978 A | 2/1989 | Schmit et al. | |

(Continued)

FOREIGN PATENT DOCUMENTS

GB          907087 A        10/1962

OTHER PUBLICATIONS

Royal Global Energy "C3+ & C4 Cut & C5 & C9" 2023, pp. 1-4 (Year: 2023).*

(Continued)

*Primary Examiner* — In Suk C Bullock
*Assistant Examiner* — Alyssa L Cepluch
(74) *Attorney, Agent, or Firm* — Gary M. Machetta

(57) ABSTRACT

A first stream containing 1,3-butadiene, $C_4$ acetylenes, and optionally $C_3$ hydrocarbons, is mixed with a portion of the liquid recycle stream from a $C_4$ acetylene hydrogenation reactor containing hydrogenated $C_4$ acetylenes and a molecular hydrogen-containing stream, the resulting mixed stream is then fed to a $C_4$ acetylene hydrogenation reactor to selectively hydrogenate the $C_4$ acetylenes in the crude butadiene stream without appreciable 1,3-butadiene conversion.

7 Claims, 2 Drawing Sheets

(51) Int. Cl.
*C07C 5/09* (2006.01)
*C07C 11/167* (2006.01)

(56) References Cited

U.S. PATENT DOCUMENTS

| | | | |
|---|---|---|---|
| 4,831,200 | A | 5/1989 | Debras et al. |
| 5,090,977 | A | 2/1992 | Strack et al. |
| 5,877,363 | A | 3/1999 | Gildert et al. |
| 6,258,989 | B1 | 7/2001 | Owen et al. |
| 6,420,619 | B1 | 7/2002 | Gartside et al. |
| 6,576,132 | B2 | 6/2003 | Kurukchi et al. |
| 7,128,827 | B2 | 10/2006 | Tallman et al. |
| 7,294,749 | B2 | 11/2007 | Verma et al. |
| 7,527,725 | B2 | 5/2009 | Viswanathan et al. |
| 7,560,019 | B2 | 7/2009 | McCoy et al. |
| 7,741,526 | B2 | 6/2010 | Kuechler et al. |
| 8,025,773 | B2 | 9/2011 | McCoy et al. |
| 9,896,395 | B2 | 2/2018 | Iaccino et al. |
| 9,969,944 | B2 | 5/2018 | Kurukchi et al. |
| 10,619,112 | B2 | 4/2020 | Al-Ghamdi |
| 2002/0128528 | A1 | 9/2002 | Pinault et al. |
| 2006/0025641 | A1 | 2/2006 | Gartside et al. |
| 2007/0264176 | A1 | 11/2007 | Stewart et al. |
| 2015/0175502 | A1 | 6/2015 | Hwang et al. |
| 2016/0332932 | A1* | 11/2016 | Montalbano ............ C07C 7/163 |
| 2017/0174585 | A1* | 6/2017 | Charra .................. B01J 8/0457 |

OTHER PUBLICATIONS

Xu, R et al., "Cyclopentadiene Dimerization Kinetics in the Presence of C5 Alkenes and Alkadienes," pates 22516-22525, Industrial and Engineering Chemistry Research, vol. 58. Sep. 5, 2019; Entire Document; DOI: 10.1021/acs.iecr.9b04018.

Gao, S. et al., "The reaction kinetics of cyclopentadiene dimerizaiton using differential scanning calorimetry: Experiments and modelling" pp. 241-246, Thermochimica Acta. vol. 589. Aug. 10, 2014; Entire Document; DOI: 10.1016/j.tca2014.05.031.

Yang, Z. et al., "Molecular dynamics of the two-stage mechanism of cyclopentadiene dimerization: concerted or stepwise?" pp. 120-125. Chemical Physics. vol. 514. Oct. 25, 2018; Entire Document; DOI: 10.1016/j.chemphys.2018.02.020.

International Searching Authority, Patent Cooperation Treaty; International Application No. PCT/US2022/026543 filed Apr. 27, 2022; International Search Report and Written Opinion dated Sep. 23, 2022; 16 pages.

* cited by examiner

UPGRADING STREAMS COMPRISING C$_3$ AND C$_4$ HYDROCARBONS

CROSS REFERENCE TO RELATED APPLICATION

This application claims priority to U.S. Provisional Patent Application having Ser. No. 63/180,311 filed on Apr. 27, 2021 which is incorporated by reference herein.

TECHNICAL FIELD

The present invention relates to upgrading a stream comprising C$_3$ and C$_4$ hydrocarbons, to processes for carrying out such upgrading, to systems for carrying out such processes, and to the upgraded product. The upgrading can include hydroprocessing a crude butadiene stream, as may be obtained from a steam cracker unit. The hydroprocessing can include the selective hydrogenation of C$_4$ acetylenes, such as the selective hydrogenation of at least a portion of any vinyl and ethyl acetylenes in the crude butadiene stream.

BACKGROUND

In a conventional steam cracking process, C$_4$ acetylenes, such as vinyl acetylenes and ethyl acetylenes, are required to be removed from the crude butadiene stream leaving as the overhead of the debutanizer, which is almost entirely made up of a mixture of C$_4$ hydrocarbons, to meet certain product specifications.

This reduction or removal of C$_4$ acetylenes from the crude butadiene stream is typically accomplished by sending the crude butadiene stream to a hydrogenation reactor in which the primarily C$_4$ hydrocarbon-containing crude butadiene stream is hydrogenated over a selective catalyst.

However, in certain configurations of a steam cracking process, the debutanizer that forms the crude butadiene stream, also known as the debutanizer overhead, is placed in sequence upstream of a depropanizer, which results in the debutanizer overhead to be comprised of a mixture of C$_3$ and C$_4$ hydrocarbons; not just C$_4$ hydrocarbons.

When trying to selectively convert C$_4$ acetylenes through hydrogenation from a stream containing both C$_4$ and C$_3$ range hydrocarbons, there is a risk that the desired selectivity and conversion of the hydrogenation catalyst will not be achieved, resulting in an increased selectivity for undesirable hydrogenation of 1,3-butadiene molecules in the crude butadiene stream and/or a decreased selectivity for desirable hydrogenation of C$_4$ acetylenes.

U.S. Pat. No. 4,831,200 discloses that alkynes are selectively hydrogenated in alkene rich hydrocarbon feeds, such as 1,3-butadiene-rich C$_4$ cuts, by passing the hydrocarbon feed at least partially in liquid phase over a palladium-based catalyst in the presence of hydrogen, preferably in trickle mode, followed by passing the effluent, at least partially in liquid phase preferably containing about 300-400 ppmw alkynes, over a copper-based catalyst in the presence of hydrogen thereby producing a hydrocarbon product of significantly reduced alkyne concentration. In other words, the '200 patent requires the use of two successive reactors with different catalysts in each.

Further, U.S. Pat. No. 5,877,363 discloses process for the removal of vinylacetylene, ethylacetylene and 1,2-butadiene from C$_4$ aliphatic hydrocarbon streams comprising, concurrently: (1) feeding hydrogen and a hydrocarbon stream comprising C$_4$ hydrocarbons including butanes, butenes, butadienes and vinylacetylene to a distillation column reactor containing a bed comprising a hydrogenation catalyst of the type characterized by platinum, palladium or rhodium which is prepared as a distillation structure to selectively hydrogenate a portion of the vinylacetylene and the 1,2-butadiene and (2) fractionally distilling the reaction mixture to remove a heavier fraction and removing a fraction overhead comprising substantially all of the C$_4$.

Both U.S. Pat. Nos. 4,831,200 and 5,877,363 refer to processes where the stream containing entirely C$_4$-range molecules are hydrogenated over a selective catalyst. There needs to be a process for C$_4$ acetylenes hydrogenation in the presence of C$_3$ hydrocarbons which also includes the presence of C$_3$ acetylenes and achieves improved selectivity.

Therefore, in one non-limiting embodiment it is desired to hydrogenate C$_4$ acetylenes in such mixed hydrocarbon streams in a manner that substantially maintains selectively and conversion for hydrogenating the C$_4$ acetylenes.

In another non-restrictive version, is particularly desired to do so hydrogenate C$_4$ acetylenes in such mixed hydrocarbon streams in a manner that gives increased selectivity and/or conversion.

Further in a different non-limiting embodiment, it is desirable to hydrogenate C$_4$ acetylenes in such mixed hydrocarbon streams with decreased hydrogenation of valuable hydrocarbons such as 1,3-butadiene and propylene.

Thus, there is a need for improvements in hydrogenation of C$_4$ acetylenes in such hydrocarbon streams, as well as systems for achieving these improvements.

SUMMARY

There is provided, in one form, a process for hydrogenating a first stream comprising (i) at least 20 wt. % of C$_3$ hydrocarbons and (ii) C$_4$ hydrocarbons including C$_4$ acetylenes and 1,3-butadiene. The process includes contacting molecular hydrogen and the first stream in a hydrogenation reactor to hydrogenate at least a portion of the first stream's C$_4$ acetylenes to form a second stream that is conducted away from the hydrogenation reactor, wherein the hydrogenation converts (1) at least 20 wt % of the first stream's C$_4$ acetylenes, and (2) less than or equal to 8 wt % of the first stream's 1,3-butadiene and/or less than or equal to 20 wt % of the first stream's C$_3$ hydrocarbon (olefins+diolefins).

Other non-restrictive forms relate to a process for selectively hydrogenating a first stream comprising (i) C$_3$ hydrocarbons and (ii) C$_4$ hydrocarbons including C$_4$ acetylenes and 1,3-butadiene.

In another non-limiting embodiment, the process includes introducing molecular hydrogen into the first stream to form a hydrogen-enriched stream, and conducting at least a portion of the hydrogen-enriched stream to a hydrogenation reactor. The molecular hydrogen-containing stream may have at least 35 wt % molecular hydrogen, alternatively at least 99 wt % molecular hydrogen, and in another non-limiting version may be substantially pure molecular hydrogen.

At least a portion of the C$_4$ acetylenes in the hydrogen-enriched stream are hydrogenated in a hydrogenation reactor to form a second stream.

The temperature at the reactor's inlet is in a range of from about 50° F. (10° C.) independently to about 140° F. (about 60° C.) from start of run to end of run, alternatively from about 78° F. (25° C.) independently to about 95° F. (35° C.). As used herein with respect to a parameter range, the word "independently" means that any range endpoint may be used together with any other range endpoint to give an acceptable alternative range. The cooler operating temperature is essential to minimizing vaporization and thus helping with the improved selectivity. Also, higher temperature drives the activity up and the butadiene loss can increase.

The $C_3$ and $C_4$ hydrocarbons should be maintained in the liquid phase. Vaporization of the $C_3$ and $C_4$ is not used to control the reactor temperature. The reactor's total pressure is at least that needed to maintain the $C_3$ and $C_4$ hydrocarbons in the liquid phase during the hydrogenation. In one non-limiting embodiment the pressure ranges from about 300 psia (about 2.1 MPa) independently to about 600 psia (about 4.9 MPa); alternatively from about 350 psia (about 2.5 MPa) independently to about 400 psia (2.8 MPa). Higher pressure is better for hydrogen solubility in feed.

In another non-restrictive version, the process also includes conducting the effluent or second stream away from the hydrogenation reactor, cooling the second stream, and separating liquid hydrocarbon from the cooled second stream.

At least a portion of the separated liquid hydrocarbon is recycled to the first stream at a recycle ratio (weight of recycled portion of the separated liquid hydrocarbon to weight of first stream) in a range of from about 0 independently to about 3; alternatively from about 0.9 independently to about 1.5.

There is additionally provided an upgraded hydroprocessed product produced by the selective hydrogenation process herein that comprises from about 0.5 independently to about 2 wt % hydrogenated $C_4$ acetylenes; alternatively from about 0.9 independently to about 1.6 wt % hydrogenated $C_4$ acetylenes. Additionally, the upgraded hydroprocessed product has from about 20 wt % independently to about 60 wt % hydrogenated 1,3-butadiene; alternatively from about 40 independently to about 50 wt % hydrogenated 1,3-butadiene. The upgraded hydroprocessed product may also have from about 20 wt % independently to about 60 wt % of hydrogenated $C_3$ hydrocarbons; alternatively from about 40 wt % independently to about 50 wt % of hydrogenated $C_3$ hydrocarbons.

In yet other forms, a hydroprocessed product is provided, as are methods for making the hydroprocessed product. Systems for carrying out any of the foregoing processes and methods are within the scope of the invention. For instance, there is additionally provided an ethylene plant having a gas cracker having a crude product effluent; a debutanizer in fluid communication with the crude product effluent, the debutanizer comprising a debutanizer overhead reflux drum containing mixed $C_3$s and $C_4$s with the $C_4$s including undesirable $C_4$ acetylenes and desirable butadiene; a pump in fluid communication with crude butadiene in a first stream from the debutanizer overhead reflux drum through a heat exchanger to a hydrogenation reactor; a molecular hydrogen-containing stream in fluid communication with the first stream; an effluent line from the hydrogenation reactor directing an effluent stream through the heat exchanger to a recycle drum; a recycle line in communication with the first stream; and a hydrogenated product stream in fluid communication with the recycle line.

DETAILED DESCRIPTION

It has been discovered that mixing a crude butadiene stream containing 1,3-butadiene, propylene, and $C_4$ hydrocarbons, and optionally $C_3$ hydrocarbons, with a molecular hydrogen-containing stream before feeding the resulting stream to the $C_4$ acetylene hydrogenation reactor may preserve selectively for the hydrogenation of the $C_4$ acetylenes in the stream while avoiding an increase in the loss of 1,3-butadiene and propylene in the stream.

In one embodiment, the $C_4$ and $C_3$ hydrocarbons in the stream may be a mixture of saturates, olefins, diolefins, and acetylenes. Example feed conditions of the $C_4$ acetylenes and hydrogen ($H_2$) feed are provide in Table Y below along with operating conditions.

TABLE Y

| Feed conditions | | |
|---|---|---|
| Operating conditions | | |
| Pressure, psia (MPa) | 340 (2.3) | |
| Temperature (inlet), F. | 93 | |
| Feed, lb/hr (kg/hr) | 1 (0.45) | |
| H2, lb/hr (g/hr) | 0.0007 (0.318) | |
| Components | $C_4$ acetylenes reactor feed wt % | $H_2$ wt % |
| Hydrogen | 0.01 | 100 |
| Ethane | 0.04 | |
| Methyl Acetylene | 0.6 | |
| Propadiene | 0.4 | |
| Propylene | 41 | |
| Propane | 7 | |
| Vinyl Acetylene | 0.7 | |
| 1-Butyne | 0.1 | |
| 1,3-Butadiene | 38 | |
| 1-Butene | 4 | |
| Cis-2-Butene | 1 | |
| Trans-2-Butene | 1 | |
| Isobutylene | 0.2 | |
| n-Butane | 6 | |
| 3-Methyl-1-Butene | 0.1 | |
| Total | 100 | 100 |

The hydrogenation catalyst(s) useful for hydrogenating the $C_4$ acetylenes in the stream may be, without limitation, palladium-on-alumina catalysts with a proprietary component which improves vinyl acetylene conversion and selectivity. The primary reactions and possible but minor reactions are show below. Key process parameters are also provided below.

Primary Reactions

Vinyl Acetylene ($C_4H_4$)+$H_2$→Butadiene ($C_4H_6$)

Ethyl Acetylene ($C_4H_6$)+$H_2$→Butene ($C_4H_8$)

Butadiene ($C_4H_6$)+$H_2$→Butene ($C_4H_8$)

Possible but Minor Reactions

Methyl Acetylene $(C_3H_4)+H_2 \rightarrow$ Propylene $(C_3H_6)$
Propadiene $(C_3H_4)+H_2 \rightarrow$ Propylene $(C_3H_6)$
Propylene $(C_3H_6)+H_2 \rightarrow$ Propane $(C_3H_8)$

| | | |
|---|---|---|
| Operating Temp. (° C.) | 27~50 | Moderate Condition |
| LHSV | 10~20 | High Throughput |
| Pressure (MPag) | 2.2~3.9 | Avoid vaporization |
| Vinyl Acetylene Conversion | 50~80% | High Activity |
| Butadiene Loss | −1.0~−0.2% | Butadiene Gain |
| Regeneration Period | | Depends on VA in Feed |
| Regeneration | Time 1~2 Day | Air Burning Process |

Figure 1:
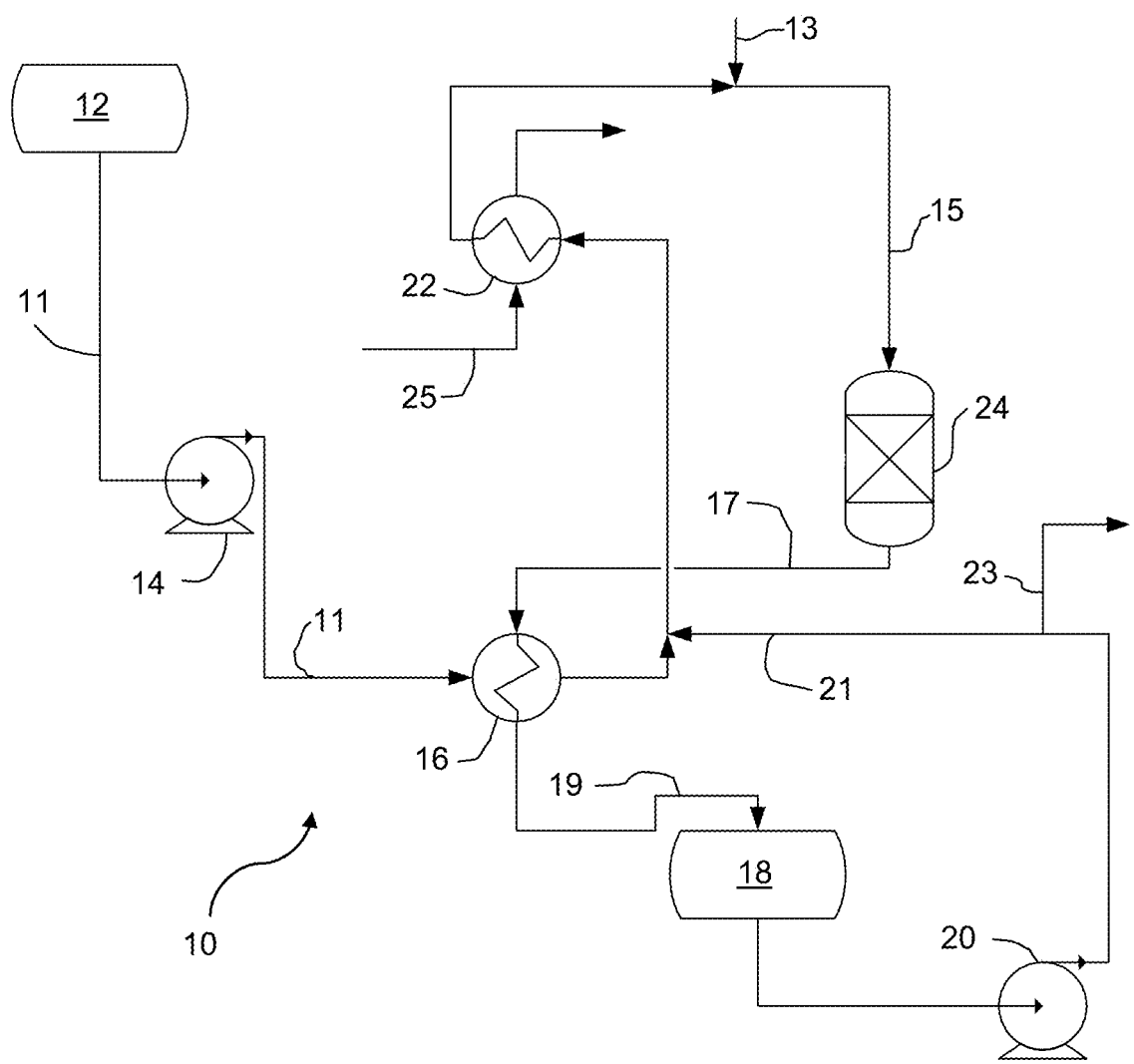
FIG. 1 is a schematic illustration of a non-limiting embodiment of a process for hydrogenation of $C_4$ acetylenes in a crude butadiene stream also containing $C_3$ hydrocarbons.

Certain forms for the selective hydrogenation of $C_4$ acetylenes contained with a crude butadiene stream comprising a mixture of a plurality of hydrocarbon compounds is shown schematically in in FIG. 1. The process and system are not limited to these forms, and this description should not be interpreted as excluding other forms within the broader scope of the process and/or system.

Referring to FIG. 1, a selective dehydrogenation process 10 is schematically shown which comprises a mixed $C_3/C_4$ product stream 11 containing 1,3-butadiene, propylene, and $C_3/C_4$ hydrocarbon mixture is pumped via pump 14 from debutanizer overhead reflux drum 12 and heated in first heat exchanger 16 to desired temperature of about 75-100° F. (about 17 to about 38° C.) in one non-limiting embodiment. It is appreciated that in another non-limiting embodiment that the pressure of the system and process should be great enough to keep hydrocarbons in liquid phase through the selective hydrogenation reactor 24, such as in the non-limiting range of about 325-375 psia (about 2.24 to 2.59 MPa). A portion of the liquid recycle stream 21 leaving the recycle drum 18 that is used to separate any vapor from the liquid in the cool reactor effluent stream 19 is combined with the mixed $C_3/C_4$ product stream 11. Pump 20 withdraws the recycle stream 21 from recycle drum 18. In one non-limiting embodiment, the recycle weight ratio of recycle stream 21 to mixed $C_3/C_4$ product stream 11 is in the range of about 0.75 to about 1.5, and will vary from the start to the end of the reactor run. This ratio may be optimized for determination of the size of the reactor and pumps, exchangers.

After the combination of mixed $C_3/C_4$ product stream 11 and 21 is heated, a molecular hydrogen-containing stream 13 is then added. This mixed reactor feed stream 15 is fed to a selective hydrogenation reactor 24 filled with suitable hydrogenation catalyst to selectively hydrogenate any $C_4$ acetylenes in the feed. Mixed reactor feed stream 15 may be heated in second heat exchanger 22 by low pressure (LP) steam 25 for startup or end-of-run conditions. A warm reactor effluent stream 17 containing the selectively hydrogenated product is conducted away from the reactor outlet, cooled, and then sent to a recycle drum 18 for vapor/liquid separation. Part of the drum liquid, recycle stream 21, is directed to be combined with mixed $C_3/C_4$ product stream 11 and the upgraded hydroprocessed mixed $C_3/C_4$ product 23 containing the upgraded hydroprocessed mixed $C_3/C_4$ product is conducted away from the process for storage and/or further processing.

Figure 2:
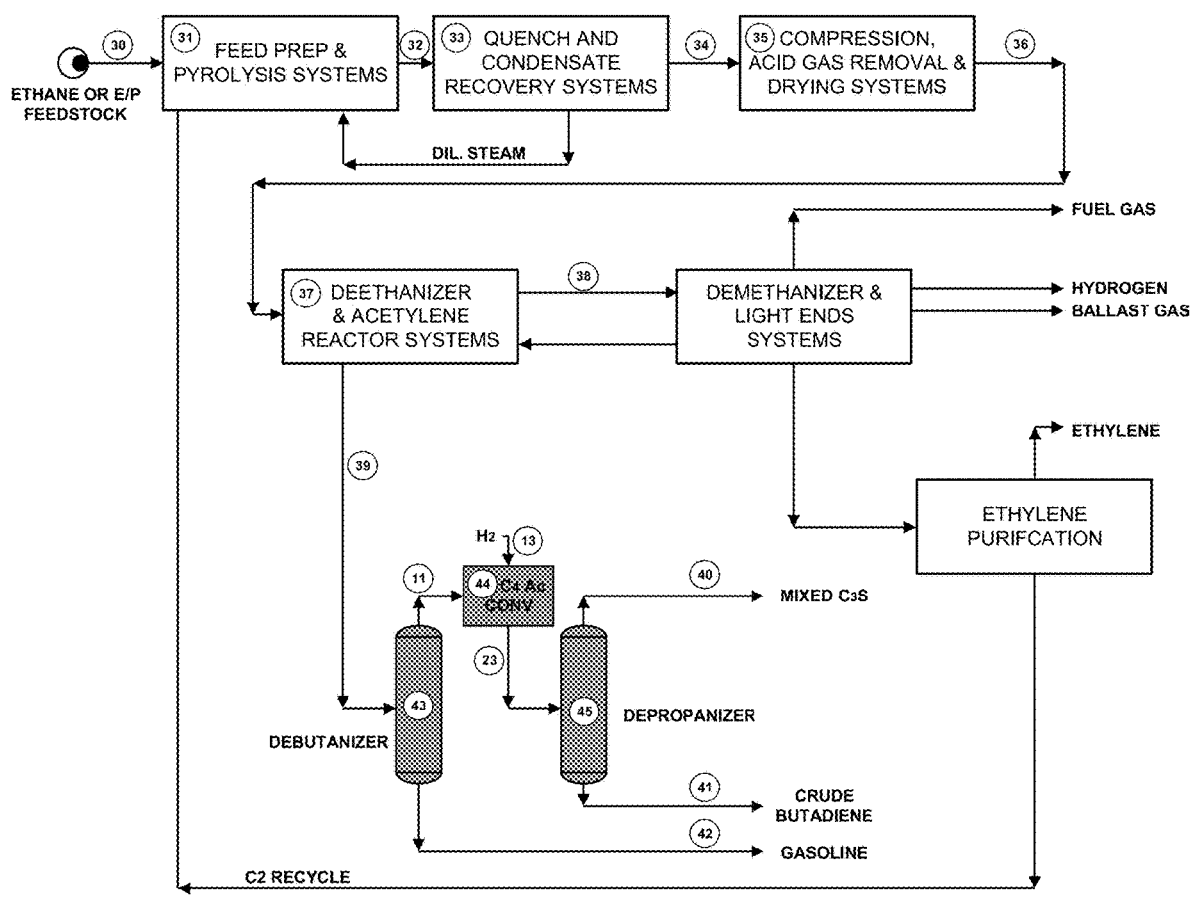
FIG. 2 is a schematic illustration of the ethane cracker showing the placement of the $C_4$ acetylenes reactor in the product recovery system.

Referring to FIG. 2, a gas cracker is shown featuring ethane feed 30 (or a mix of ethane and propane) to the Pyrolysis System 31. The cracked gas 32 passes to the Quench and Condensate Recovery System 33 where it is cooled. The cooled crack gas 34 feeds the Compression, Acid Gas Removal and Drying Systems 35. The compressed cracked gas 36 feeds the Deethanizer and Acetylene Reactor Systems 37 where the $C_2$ and lighter components 38 are separated from the $C_3$ and heavier components 39. The $C_3$ and heavier components 39 make up three products that have value: a propylene-rich mixed $C_3$s product 40, a crude butadiene product 41, and a pyrolysis gasoline product 42.

Producing the crude butadiene product normally would have the $C_3$ and heavier components feed a Depropanizer, with the bottoms then feeding a Debutanizer to produce a mixed $C_4$s product on the Debutanizer overhead. The Debutanizer overhead can then be treated in a $C_4$ Acetylene Reactor System provided to upgrade the crude butadiene product as the reduction or elimination of acetylenes can yield higher market value for the product stream or it could result in savings in a butadiene unit that exceed the cost of the $C_4$ Acetylene Reactor System. However the $C_4$ Acetylene Reactor System adds light end contaminants that would need to be removed by an additional Stripper System.

FIG. 2 shows resequencing operations to feed the C3 and heavier components to a Debutanizer 43 first, with the overhead mixed C3s and C4s crude butadiene 11 then feeding the C4 Acetylene Reactor System 44. The mixed C3/C4 product stream 11 then react with molecular hydrogen-containing stream 13 to achieve the targeted reactions. The upgraded hydroprocessed mixed C3/C4 liquid 23 containing light end contaminants can then feed the Depropanizer 45 which will separate out the Crude Butadiene 41 as the Depropanizer bottoms. This eliminates the Stripper System required in the conventional configuration.

An additional benefit of the reconfigured system is that $C_4$ Acetylene Reactor System 44 operates at milder conditions which improve selectivity of the hydrogenation reactions as discussed above.

It is appreciated that conversion of $C_4$ acetylenes can be targeted to meet the specifications for $C_4$ acetylenes in the product crude butadiene stream. This is accomplished by controlled injection of hydrogen to hydrogenate $C_4$ acetylenes selectively. The reactor size, recycle rate, pressure, and temperature of reactor inlet may be designed to achieve or exceed the desired conversion of $C_4$ acetylenes and to decease or even minimize conversion of the 1,3-butadiene and propylene present in the crude butadiene stream. In one exemplary embodiment, the desired run length may be in the range of about 2 months independently to about 12 months; alternatively from about 6 independently to about 9 months; and the range of space velocity (LHSV) may be in the range of 4 independently to about 20; alternatively from about 8 independently to about 16.

It will also be appreciated that any hydrogenation of $C_3$ acetylenes, such as methyl acetylene and propadiene, in this process, though not intended, is beneficial.

The processes and systems described herein may accomplish a variety of goals including, but not necessarily limited to: hydrogenating $C_4$ acetylenes in mixed hydrocarbon streams in a manner that substantially maintains selectively and conversion for hydrogenating the $C_4$ acetylenes; hydrogenating $C_4$ acetylenes in mixed hydrocarbon streams in a manner that gives increased selectivity and/or conversion; and hydrogenating $C_4$ acetylenes in mixed hydrocarbon streams with decreased hydrogenation of valuable hydrocarbons such as 1,3-butadiene and propylene. The processes and systems described herein are considered effective and successful even if only one of these goals is accomplished, such as achieving substantially the selectivity and conversion of $C_4$ acetylenes in a mixed $C_3/C_4$ stream with a $C_4$ stream. The processes and systems may be considered even more effective if one or more of the other goals is/are also achieved.

In the foregoing specification, the invention has been described with reference to specific embodiments thereof. However, the specification is to be regarded in an illustrative rather than a restrictive sense. For example, hydrocarbons, catalysts, hydrogenation reaction conditions and equipment, and composition and conditions of various streams falling within the claimed or disclosed parameters, but not specifically identified or tried in a particular example, are within the scope of this invention.

The present invention may be practiced in the absence of a feature not disclosed. In addition, the present invention may suitably comprise, consist or consist essentially of the elements disclosed. For instance, the process may comprise, consist of, or consist essentially of contacting a crude butadiene stream comprising 1,3-butadiene, propylene, and other $C_4$ and $C_3$ hydrocarbons with a portion of a liquid recycle stream containing hydrogenated $C_4$ acetylenes and with a molecular hydrogen-containing stream to form a mixed feed stream, sending the mixed feed stream to a hydrogenation reactor to hydrogenate the $C_4$ acetylene in the mixed feed stream to form an effluent stream containing hydrogenated $C_4$ acetylenes, sending the effluent stream to a drum for vapor-liquid separation to separate any vapor from the liquid stream containing hydrogenated $C_4$ acetylenes.

The words "comprising" and "comprises" as used throughout the claims, are to be interpreted to mean "including but not limited to" and "includes but not limited to", respectively.

To the extent used herein, the word "substantially" shall mean "being largely but not wholly that which is specified."

As used herein, the singular forms "a," "an," and "the" are intended to include the plural forms as well, unless the context clearly indicates otherwise.

To the extent used herein, the term "about" in reference to a given parameter is inclusive of the stated value and has the meaning dictated by the context (e.g., it includes the degree of error associated with measurement of the given parameter).

To the extent used herein, the term "and/or" includes any and all combinations of one or more of the associated listed items.

What is claimed is:

1. A selective hydrogenation process, comprising:
   providing a first stream comprising hydrocarbon compounds, wherein the first stream comprises:
   at least 20 wt. % of C3 hydrocarbons; and
   $C_4$ hydrocarbons comprising $C_4$ acetylenes and 1,3-butadiene;
   contacting the first stream with a recycle portion of a liquid stream containing hydrogenated $C_4$ acetylenes and with a molecular hydrogen-containing stream to form a mixed feed stream, wherein the mixed feed stream comprises:
   (i) one or more the $C_3$ hydrocarbon compounds, and
   (ii) $C_4$ hydrocarbon compounds including the $C_4$ acetylenes and the 1,3-butadiene;
   sending the mixed feed stream to a hydrogenation reactor to hydrogenate at least a portion of the $C_4$ acetylenes to form an effluent stream containing hydrogenated $C_4$ acetylenes;
   separating the liquid stream containing hydrogenated $C_4$ acetylenes from the effluent stream; and
   removing from the liquid stream the recycle portion of the liquid stream containing hydrogenated $C_4$ acetylenes.

2. The selective hydrogenation process of claim 1, wherein the mixed feed stream comprises propylene.

3. The selective hydrogenation process of claim 1, wherein the hydrogenation of at least a portion of the $C_4$ acetylenes is conducted at a pressure great enough to keep the hydrocarbons in liquid phase.

4. The selective hydrogenation process of claim 3, wherein the pressure ranges from about 320 psia (about 2.2 MPa) to about 565 psia (about 3.9 MPa).

5. The selective hydrogenation process of claim 1, wherein the hydrogenation reactor has an inlet, and where the temperature at the inlet ranges from about 80° F. (27° C.) to about 122° F. (about 50° C.).

6. The selective hydrogenation process of claim 1, wherein the hydrogenation converts:
   (1) at least 45 wt % of the $C_4$ acetylenes of the first stream; and
   (2) at least one of:
      (a) at least 10 wt % of the 1,3-butadiene of the first stream,
      (b) less than or equal to 10 wt % of the $C_3$ hydrocarbon of the first stream, or
      (c) a combination of (a) and (b).

7. The selective hydrogenation process of claim 1, wherein a recycle ratio of weight of the recycled portion of the liquid stream to weight of the first stream ranges from about 0.75 to about 1.5.

* * * * *